(12) United States Patent
Nappa et al.

(10) Patent No.: US 9,000,241 B2
(45) Date of Patent: Apr. 7, 2015

(54) USE OF COPPER-NICKEL CATALYSTS FOR DEHLOGENATION OF CHLOROFLUOROCOMPOUNDS

(75) Inventors: Mario Joseph Nappa, Newark, DE (US); Ekaterina N. Swearingen, Wilmington, DE (US); Allen Capron Sievert, Elkton, MD (US); Xuehui Sun, Swedesboro, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 508 days.

(21) Appl. No.: 13/277,268

(22) Filed: Oct. 20, 2011

(65) Prior Publication Data

US 2012/0108859 A1    May 3, 2012

Related U.S. Application Data

(60) Provisional application No. 61/409,260, filed on Nov. 2, 2010.

(51) Int. Cl.
| | | |
|---|---|---|
| C07C 17/00 | (2006.01) | |
| C07C 17/25 | (2006.01) | |
| C07C 17/23 | (2006.01) | |

(52) U.S. Cl.
CPC ............ C07C 17/25 (2013.01); C07C 17/23 (2013.01)

(58) Field of Classification Search
CPC ...... C07C 21/18; C07C 17/25; C07C 17/206; C07C 19/10; C07C 19/08; C07C 17/23; C07C 17/087; C07C 17/383; C07C 17/21; C07C 19/01; C07C 17/278; C07C 17/354; C07C 17/04; C07C 17/204; C07C 17/42
USPC .................................................. 570/153, 156
See application file for complete search history.

(56) References Cited

U.S. PATENT DOCUMENTS

| | | | |
|---|---|---|---|
| 2,697,124 A * | 12/1954 | Mantell | ........................ 570/157 |
| 2,900,423 A | 8/1959 | Smith | |
| 3,505,417 A | 4/1970 | Gardner | |
| 6,540,933 B1 | 4/2003 | Sievert et al. | |
| 2008/0027251 A1 * | 1/2008 | Nair et al. | ..................... 570/176 |

FOREIGN PATENT DOCUMENTS

| | | |
|---|---|---|
| CN | 101356143 A | 1/2009 |
| WO | 2007/019355 A1 * | 2/2007 |

OTHER PUBLICATIONS

Satterfield, Heterogeneous Catalysis in Industrial Practice, 2nd Edition, pp. 87-112, McGraw-Hill, New York, 1991.
Boudart, Decomposition of Formic Acid on Copper, Nickel and Copper-Nickel Alloys, Journal of Catalysis, 1983, 81, 201-213.
U.S. Appl. No. 61/409,260, filed Nov. 2, 2010.
Gang, Y., et al. "The study progress of HFO-1234yf synthesis" Organo Fluorine Industry, vol. 3, p. 12-15 (2009) (in Chinese).
Xia, L., et al. "The study of the production technique of 2, 3, 3, 3-tetrafluoropropyl (HFO-1234yf)" Organo Fluorine Industry, vol. 4, p. 38-41 (2008) (in Chinese).
Chinese Office Action and First Search Report dated May 9, 2014, issued in Chinese Application No. 201180063722.6 (in Chinese and in English).

* cited by examiner

*Primary Examiner* — Jafar Parsa
(74) *Attorney, Agent, or Firm* — Scully, Scott, Murphy & Presser, P.C.

(57) ABSTRACT

The disclosure describes a process for dehalogenation of chlorofluorocompounds. The process comprises contacting a saturated chlorofluorocompound with hydrogen in the presence of a catalyst at a temperature sufficient to remove chlorine and/or fluorine substituents to produce a fluorine containing terminal olefin.

23 Claims, No Drawings

__USE OF COPPER-NICKEL CATALYSTS FOR DEHLOGENATION OF CHLOROFLUOROCOMPOUNDS__

CROSS REFERENCE(S) TO RELATED APPLICATION(S)

This application claims the priority benefit of U.S. Provisional Application No. 61/409,260, filed Nov. 2, 2010.

FIELD OF THE DISCLOSURE

The present invention is in the field of synthesis of fluorinated olefins.

BACKGROUND OF THE INVENTION

The fluorocarbon industry has been working for the past few decades to find replacement refrigerants for the ozone depleting chlorofluorocarbons (CFCs) and hydrochlorofluorocarbons (HCFCs) that are being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a, and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well having low global warming potentials. Certain hydrofluoroolefins are believed to meet both goals. There is a need for manufacturing processes that provide halogenated hydrocarbons and fluoroolefins that contain no chlorine that also have a low global warming potential.

SUMMARY OF THE INVENTION

The present invention provides a process for dehalogenation of chlorofluorocompounds. The process comprises contacting a saturated chlorofluorocompound with hydrogen in the presence of a catalyst at a temperature sufficient to remove chlorine and/or fluorine substituents to produce a fluorine containing terminal olefin.

DETAILED DESCRIPTION OF ILLUSTRATIVE EMBODIMENTS

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and b are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Further, reference to values stated in ranges include each and every value within that range.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publication, patent applications, patents, and other references mentioned herein are incorporated by reference in their entirety, unless a particular passage is cited. In case of conflict, the present specification, including definitions, will control. In addition, the materials, methods, and examples are illustrative only and not intending to be limiting.

Many aspects and embodiments are described herein, and are merely exemplary, not limiting. After reading this specification, skilled artisans will appreciate that other aspects and embodiments are possible without departing from the scope of the invention. Other features and benefits of any one or more of the embodiments will be apparent from the following detailed description, and from the claims.

The present invention is directed to a process for producing a fluorine containing terminal olefin. As used herein, a fluorine containing terminal olefin refers to a fluorine containing olefin, wherein one end of the double bond is a $CH_2$ group. According to one aspect of the present invention, a process is provided for the dehalogenation of chlorofluorocompounds comprising contacting a saturated chlorofluorocompound with hydrogen in the presence of a catalyst. The temperature of the reaction is sufficient to remove chlorine and fluorine substituents.

The chlorofluorocompound has the following formula: $R_fCFX^1CH_2X^2$, wherein $R_f$ is a fluoroalkyl group selected from $CF_3$, $C_2F_5$, $CHF_2$, and $C_3F_7$; $X^1$ is selected from F and Cl; and $X^2$ is selected from Cl, Br, and I.

Catalysts containing copper, nickel, chromium, palladium, and ruthenium are known in the art. They may be prepared by either precipitation methods or impregnation methods as generally described by Satterfield on pages 87-112 in *Heterogeneous Catalysis in Industrial Practice*, $2^{nd}$ edition (McGraw-Hill, New York, 1991), the disclosure of which is incorporated herein by reference. Embodiments of the present invention include catalysts that dehalogenate the chlorofluorocompounds as opposed to those that merely result in hydrogenolysis or hydrogenation.

In one embodiment, the catalyst comprises nickel, copper, or combinations thereof. In one embodiment the catalyst comprises copper and nickel. In one embodiment, the catalyst may further comprise chromium. In yet another embodiment, the catalyst comprises nickel and chromium.

In some embodiments, the catalysts of this invention may contain other components, some of which are considered to improve the activity and/or longevity of the catalyst composition. Such catalysts include catalysts which are promoted with compounds of potassium, cesium, rubidium, or combinations thereof. Without wishing to be bound to any particular theory, alkali metal promoters are believed to reduce the rate of decline of catalyst activity over time.

The catalyst may be supported or unsupported. Supports such as metal fluorides, alumina and titania may be advantageously used. In one embodiment, the catalyst supports are fluorides of metals of Group II, including magnesium fluoride, calcium fluoride, strontium fluoride and barium fluoride. In one embodiment, the support is calcium fluoride. In one embodiment, a catalyst consists essentially of copper, nickel and chromium oxides (each of said oxides being preferably present in equimolar quantities) promoted with a potassium salt, on calcium fluoride.

In some embodiments, the catalyst is selected from copper on carbon, copper on calcium fluoride, copper and nickel on carbon, nickel on carbon, copper/nickel/chromium on calcium fluoride, or unsupported alloys of copper and/or nickel. In other embodiments, the catalyst may be Rhenium on carbon and Ruthenium on carbon. In certain embodiments, the amount of carbon or calcium fluoride support is from about 30% by weight to about 99.9% by weight. In other embodiments, the carbon support may be acid washed.

In one embodiment, copper and nickel on carbon may contain from about 1% to about 25% by weight copper and nickel combined on the carbon support. The carbon support may be any of the carbon supports as described herein for other catalysts. The weight ratio of the copper to nickel in the copper and nickel on carbon catalyst may range from about 2:1 to about 1:2.

In one embodiment, the molar ratio of copper:nickel:chromium oxide in the copper/nickel/chromium on calcium fluoride catalyst is from about 0 to about 1 copper; from about 0.5 to about 3 nickel; and from about 0 to about 2 chromium. Preparation of the copper/nickel/chrome catalyst is described in U.S. Pat. No. 2,900,423, the disclosure of which is incorporated herein by reference.

In one embodiment, a catalyst contains proportionally about 1.0 mole CuO, about 0.2 to 1.0 mole NiO, about 1 to 1.2 moles $Cr_2O_3$ on about 1.3 to 2.7 moles $CaF_2$, promoted with about 1 to 20 wt %, based on the total catalyst weight, of an alkali metal selected from K, Cs, and Rb. In one embodiment, when K is the promoter, the amount is from about 2 to 20 wt % of the total catalyst. In another embodiment, the amount of alkali metal is from about 5 to 15 wt %. Without being bound by any particular theory, it is believed that additional of an alkali metal promoter to a catalyst composition for the production of fluorine-containing alkenes increases the selectivity for the production of the alkene, but at the same time reduces the overall conversion of starting material, especially at higher levels of alkali metal.

The unsupported alloys of copper and nickel include those described by Boudart in *Journal of Catalysis*, 81, 201-13, 1983, the disclosure of which is herein incorporated by reference. In one embodiment, the mole ratio of Cu:Ni in the catalysts may range from about 1:99 to about 99:1. In another embodiment, the mole ratio of Cu:Ni is from about 1:2 to about 2:1. In yet another embodiment, the mole ratio of Cu:Ni is about 1:1. When reference is made to alloys, it is meant a nickel alloy containing from about 1 to about 99.9 wt % nickel, or a copper alloy containing from about 1 to about 99.9 wt % copper.

In one embodiment, the catalyst can be prepared by coprecipitating, from an aqueous medium, salts of copper, nickel and chromium (and optionally aluminum and zinc), with and on calcium fluoride; washing, heating and drying the precipitate. When alkali metal carbonates are used in the precipitation process to initially produce the corresponding insoluble copper, nickel or chromium carbonates, the alkali metal counter ion may be washed away in the washing step after the carbonates are precipitated.

After precipitation, washing and drying, the precipitated catalysts are calcined. Catalysts are calcined at temperatures from 375° C. to 650° C. In some embodiments, catalysts are calcined for from 2 hours to 16 hours. In other embodiments, catalysts are calcined for from 2 hours to 8 hours. In other embodiments, catalysts are calcined for from 2 hours to 4 hours.

In embodiments where an alkali metal promoter is desired, an alkali metal compound (e.g., KOH, KF, $K_2CO_3$ or $CsCO_3$ or Rb salt) is then deposited on the dried precipitate, prior to calcination to convert the copper, nickel and chromium to the respective oxides. Any soluble copper, nickel and chromium compound may be used. In one embodiment, the copper, nickel and chromium salts are chloride or nitrates. In another embodiment, the salts are nitrates. In one embodiment, promoters such as KOH, KF, $K_2CO_3$, $CsCO_3$ or Rb salt may be added prior to co-precipitation. In one embodiment, the promoter is provided from a mixture of more than one alkali metal compound.

In one embodiment, the catalyst is granulated, pressed into pellets, or shaped into other desirable forms. The catalyst may contain additives such as binders and lubricants to help insure the physical integrity of the catalyst during granulating or scraping the catalyst into the desired form. Suitable additives include carbon and graphite. When binders and/or lubricants are added to the catalyst, they normally, comprise about 0.1 to 5 wt % of the weight of the catalyst.

In one embodiment, the catalyst is activated prior to use by treatment with hydrogen, air, or oxygen at elevated temperatures. After use for a period of time in the process of this invention, the activity of the catalyst may decrease. When this occurs, the catalyst may be reactivated by treating it with hydrogen, air or oxygen, at elevated temperature in the absence of organic materials.

In one embodiment, the molar ratio of hydrogen to organic feed for the dehalogenation reaction ranges from about 0.5:1 to about 10:1. In another embodiment, the molar ratio of hydrogen to organic feed ranges from about 1:1 to about 6:1. In yet another embodiment, the molar ratio of hydrogen to organic feed ranges from about 1:1 to about 3:1.

In one embodiment, the process for preparation of fluorine containing olefins comprises reacting a chlorofluoroalkane with hydrogen in a reaction vessel constructed of an acid resistant alloy material. Such acid resistant alloy materials include stainless steels, high nickel alloys, such as Monel, Hastelloy, and Inconel. In one embodiment, the reaction takes place in the vapor phase.

In one embodiment of the invention, the process is conducted at a temperature of from about 200° C. to about 450° C. In another embodiment of the invention, the process is conducted at a temperature of from about 300° C. to about 400° C. In yet another embodiment of the invention, the process is conducted at a temperature of from about 325° C. to about 375° C.

In one embodiment, at normally employed temperatures, the reaction contact time is typically between about 20 seconds and about 90 seconds. In another embodiment, the reaction contact time varies from about 20 seconds to about 60 seconds. In yet another embodiment, the reaction contact time varies from about 30 to about 60 seconds. In one embodiment, the reaction products may be recovered from the reaction zone by use of a suitable conventional means, such as by filtration and/or distillation. As used herein, a reaction zone may be a reaction zone may be a reaction vessel fabricated from nickel, iron, titanium or their alloys, as described in U.S. Pat. No. 6,540,933, the disclosure of which is incorporated herein by reference.

In one embodiment of the invention, the fluorochloropound comprises 3-chloro-1,1,1,2,2,-pentafluoropropane ("235ca"), wherein 2,3,3,3-tetrafluoro-1-propene ("1234yf") is produced. In another embodiment of the invention, the chlorofluorocompound comprises 2,3,-dichloro-1,1,1,2-tetrafluoropropane ("234ba"), wherein 2,3,3,3-tetrafluoro-1-propene ("1234yf") is produced. In yet another embodiment of the invention, the chlorofluorocompound comprises 3-chloro-1,1,2,2,-tetrafluoropropane ("244ca"), wherein 2,3,3-trifluoro-1-propene ("1243yf") is produced.

Benefits, other advantages, and solutions to problems have been described above, with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Further, reference to values stated in ranges include each and every value within that range.

EXAMPLES

The concepts described herein will be further described in the following examples, which do not limit the scope of the invention described in the claims. Note that not all of the activities described above in the general description or the examples are required, that a portion of a specific activity may not be required, and that one or more further activities may be performed in addition to those described. Still further, the order in which activities are listed are not necessarily the order in which they are performed.

Example 1

In Examples 1, 2, and 3, the dehalogenation catalyst may be Cu/Ni/Cr/CaF$_2$ or Cu/Ni unsupported (as depicted in the preparation described in The Journal of Catalysis 81,204-13, 1983). The starting concentrations of 235ca, 234ba and 244ca were made by reaction of corresponding alcohol with SOCl$_2$.

Example 1 demonstrates the conversion of 235ca into 1234yf over the Cu/Ni catalyst. The catalyst was made as described by E. Iglesia et al. in the *Journal of Catalysis* 81, 204-213 (1983).

115 g (0.48 mole) of Cu(NO$_3$)$_2$*4H$_2$O was dissolved in 250 ml of water, 145.5 g (0.5 mole) of Ni(NO$_3$)$_2$*6H$_2$O was dissolved in 250 ml H$_2$O mixed together and added to 174 g (2.2 g) of NH$_4$HCO$_3$ dissolved in 2 L H$_2$O. The resulting slurry was stirred for 1 hour, settled overnight, and filtered with a paper filter. Solids were placed in a beaker with 2 L of water, stirred and filtered again. The mixed carbonates were dried in a vacuum at 90° C. for 24 hours. Then, they were crushed and calcined in air at 400° C. for 2 hours. Next, they were recrushed, placed into a furnace, and reduced by the following regime: (1) furnace temperature was ramped from room temperature to 260° C. in He; (2) H$_2$ concentration was increased to pure H$_2$ over 4 hours; and (3) the temperature was then increased to 350° C. and reduction was carried out for 16 hours.

The samples were passivated by cooling to room temperature in flowing He, then gradually increasing the concentration of O$_2$ in the He stream over 2 hours. As a result, 46 g of black powder was made. The powder was pressed and pelletized to 12-20 mesh size.

A Hastelloy reactor, measuring 15"L×1" O.D.×0.074" wall, was filled with 10 cc (25 g) of Cu/Ni catalyst. The catalyst was conditioned at 50 sccm (8.3×10$^{-7}$ m$^3$/sec) hydrogen flow at 350° C. The dehalogenation of 235ca was studied at a temperature range between 325° C.-375° C. and the products indicated in Table 1. Products of the reaction were analyzed by gas chromatography-mass spectrometry ("GCMS") to give the molar concentrations as listed in Table 1.

TABLE 1

| H$_2$/235ca ratio | Contact Time, sec | Temp ° C. | fluorohydrocarbons | 1234yf | 235ca |
|---|---|---|---|---|---|
| 6:1 | 50 | 325 | 0.05 | 16.81 | 83.14 |
| 6:1 | 50 | 375 | 1.44 | 35.88 | 62.88 |

Example 2

Example 2 demonstrates the conversion of 234ba into 1234yf over Cu/Ni catalyst.

A Hastelloy reactor, measuring 15"L×1" O.D.×0.074" wall, was filled with 10 cc (25 g) of Cu/Ni catalyst. The catalyst was conditioned at 50 sccm (8.3×10$^{-7}$ m$^3$/sec) hydrogen flow at 350° C. The dehalogenation of 234bb was studied at a temperature range between 325° C.-350° C. and the products indicated in Table 2. Products of the reaction were analyzed by GCMS to give the molar concentrations as listed in Table 2.

TABLE 2

| H$_2$/23ba ratio | Contact Time, sec | Temp ° C. | fluorohydrocarbons | 1234yf | 234ba |
|---|---|---|---|---|---|
| 3:1 | 50 | 325 | 2.3 | 73.38 | 24.32 |
| 3:1 | 50 | 350 | 1.8 | 80.2 | 18.0 |

Example 3

Example 3 demonstrates the conversion of 244ca into 1243yf over Cu/Ni catalyst.

A Hastelloy reactor, measuring 15"L×1" O.D.×0.074" wall, was filled with 10 cc (25 g) of Cu/Ni catalyst. The catalyst was conditioned at 50 sccm (8.3×10$^{-7}$ m$^3$/sec) hydrogen flow at 350° C. The dehalogenation of 244ca was studied at a temperature range between 325° C.-375° C. and the products indicated in Table 3. Products of the reaction were analyzed by GCMS to give the molar concentrations as listed in Table 3.

TABLE 3

| H$_2$/244ca ratio | Contact Time, sec | Temp ° C. | fluorohydrocarbons | 254cb | 1234yf | 244ca |
|---|---|---|---|---|---|---|
| 3:1 | 50 | 325 | 0.12 | 0.16 | 20.09 | 79.63 |
| 3:1 | 50 | 350 | 0.33 | 0.7 | 30.85 | 68.12 |

Example 4

Example 4 demonstrates the conversion of 234ba into 1234yf over 10 wt % Cu/C catalyst. 10 cc 10 wt % Cu on acid washed carbon catalyst granules was loaded into a ½ inch Hastelloy C reactor. The catalyst was conditioned at 250° C. with 50 ccm/min H₂ for 2 hours. The hydrodechlorination of 234ba was studied at a temperature range of 200° C.-300° C. and the products indicated in Table 4. Products of the reaction were analyzed by GC-MS to give the GC-MS area % as listed in Table 4.

TABLE 4

| Temp | H₂/234ba | Contact Time, | GC-MS area % | |
|---|---|---|---|---|
| ° C. | mole ratio | sec | 1234yf | 234ba |
| 200 | 1.2:1 | 30 | 5.55% | 94.05% |
| 199 | 1.2:1 | 30 | 2.71% | 97.13% |
| 250 | 1.2:1 | 30 | 11.17% | 88.47% |
| 249 | 1.2:1 | 30 | 7.64% | 92.03% |
| 299 | 1.2:1 | 30 | 45.56% | 52.92% |
| 300 | 1.2:1 | 30 | 41.76% | 56.63% |

Example 5

Example 5 demonstrates the conversion of 234ba into 1234yf over 5 wt % Ru/C catalyst. 10 cc 10 wt % Ru on acid washed carbon catalyst granules was loaded into a ½-inch Hastelloy C reactor. The catalyst was conditioned at 250° C. with 50 ccm/min H₂ for 2 hours. The hydrodechlorination of 234ba was studied at a temperature range of 100° C.-200° C. and the products indicated in Table 5. Products of the reaction were analyzed by GC-MS to give the GC-MS area % as listed in Table 5.

TABLE 5

| Temp | H₂/234ba | Contact Time, | GC-MS area % | | | |
|---|---|---|---|---|---|---|
| ° C. | mole ratio | sec | 1234yf | 254eb | 263fb | 234ba |
| 98 | 1.2:1 | 30 | 1.41% | 1.61% | 0.18% | 95.04% |
| 99 | 1.2:1 | 30 | 1.76% | 1.28% | 0.15% | 96.82% |
| 123 | 1.2:1 | 30 | 5.40% | 2.22% | 0.36% | 92.03% |
| 124 | 1.2:1 | 30 | 5.12% | 18.86% | 2.27% | 73.75% |
| 156 | 1.2:1 | 30 | 25.86% | 4.58% | 1.09% | 68.26% |
| 152 | 1.2:1 | 30 | 25.39% | 4.10% | 0.95% | 69.37% |
| 172 | 1.2:1 | 30 | 69.41% | 6.22% | 1.91% | 21.86% |
| 173 | 1.2:1 | 30 | 67.35% | 4.65% | 1.40% | 26.05% |
| 200 | 1.2:1 | 30 | 73.17% | 13.81% | 11.05% | 0.00% |
| 202 | 1.2:1 | 30 | 82.55% | 9.34% | 5.98% | 0.00% |

Comparative Example 1

Comparative Example 1 shows a comparison example of 234ba converted to 254eb instead of 1234yf over 2000 ppm Pd/K/Al₂O₃ catalyst. 2000 ppm Pd/Al₂O₃ was doped with 1000 ppm potassium to reduce its activity. 10 cc catalyst granules was loaded into a ½-inch Hastelloy C reactor. The catalyst was conditioned at 250° C. with 50 ccm/min H₂ for 2 hours. The hydrodechlorination of 234ba was studied at a temperature range of 150° C.-200° C. and the products indicated in Table 6. Products of the reaction were analyzed by GC-MS to give the GC-MS area % as listed in Table 6.

Comparative Example 1 indicates an unsuccessful reaction over a Pd/Al₂O₃ catalyst. With the exception of the reaction products at 198° C. and 200° C., the highest temperature points, this particular catalyst does not dehalogenate, instead it produces hydrogenolysis of the chlorines to replace them with hydrogens.

TABLE 6

| Temp | H₂/234ba | Contact Time, | GC-MS area % | | | |
|---|---|---|---|---|---|---|
| ° C. | mole ratio | sec | 1234yf | 254eb | 244bb | 234ba |
| 149 | 1.2:1 | 30 | 0.00% | 33.90% | 0.69% | 64.63% |
| 148 | 1.2:1 | 30 | 0.00% | 37.52% | 0.76% | 61.11% |
| 152 | 1.2:1 | 30 | 0.00% | 24.89% | 0.49% | 74.30% |
| 156 | 1.2:1 | 30 | 0.00% | 22.95% | 0.45% | 76.17% |
| 198 | 1.2:1 | 30 | 3.89% | 54.67% | 1.36% | 39.37% |
| 200 | 1.2:1 | 30 | 3.79% | 52.17% | 1.34% | 42.05% |

What is claimed:

1. A process for dehalogenation of chlorofluorocompounds comprising contacting a saturated chlorofluorocompound with hydrogen in the presence of a catalyst at a temperature sufficient to remove chlorine or fluorine substituents to produce a fluorine containing terminal olefin wherein the catalyst is effective for dehalogenation of chlorofluorocompounds and wherein said chlorofluorocompound comprises a chlorofluorocompound having the formula:

$$R_fCFX^1CH_2X^2$$

wherein $R_f$ is a fluoroalkyl group selected from $CF_3$, $C_2F_5$, $CHF_2$, and $C_3F_7$;
$X^1$ is selected from F and Cl; and
$X^2$ is selected from Cl, Br, and I, wherein said catalyst is selected from copper on carbon, copper on calcium fluoride, copper and nickel on carbon, nickel and carbon, copper/nickel/chromium on calcium fluoride, unsupported alloys of copper and nickel, ruthenium on carbon, and rhenium on carbon.

2. The process of claim 1, wherein said catalyst comprises nickel, copper, or combinations thereof.

3. The process of claim 2, wherein said catalyst further comprises chromium.

4. The process of claim 2, wherein said catalyst further comprises an alkali metal selected from potassium and cesium and rubidium.

5. The process of claim 2, wherein said catalyst is unsupported alloys of copper and nickel having a molar ratio of copper:nickel of from about 1 to about 2 copper, and from about 2 to about 1 nickel.

6. The process of claim 4, wherein said catalyst is copper/nickel/chromium on calcium fluoride having a molar ratio of copper:nickel:chromium of about 0 to about 1 copper; from about 0.5 to about 3 nickel; and from about 0 to about 2 chromium.

7. The process of claim 6, wherein said catalyst further comprises an alkali metal selected from potassium, cesium and rubidium.

8. The process of claim 7, wherein the amount of said alkali metal is from 2 to 20 wt % of the total weight of said catalyst.

9. The process of claim 1, wherein said chlorofluorocompound is a chlorofluorocompound having the formula $$R_fCFX^1CH_2X^2;$$

wherein $R_f$ is a fluoroalkyl group selected from $CF_3$, $C_2F_5$, $CHF_2$, and $C_3F_7$;
$X^1$ is selected from F and Cl; and
$X^2$ is selected from Cl, Br, and I.

10. The process of claim 1, wherein the process is conducted at a temperature of from about 200° C. to about 450° C.

11. The process of claim 1, wherein the process is conducted at a temperature of from about 300° C. to about 400° C.

12. The process of claim 1, wherein the process is conducted at a temperature of from about 325° C. to about 375° C.

13. The process of claim 1, wherein the molar ratio of hydrogen to the chlorofluorocompound is from about 10:1 to about 0.5:1.

14. The process of claim 1, wherein the molar ratio of hydrogen to the chlorofluorocompound is from about 6:1 to about 1:1.

15. The process of claim 1, wherein the molar ratio of hydrogen to the chlorofluorocompound is from about 3:1 to about 1:1.

16. The process of claim 1, wherein said chlorofluorocompound comprises 3-chloro-1,1,1,2,2-pentafluoropropane.

17. The process of claim 16, wherein 2,3,3,3-tetrafluoro-1-propene is produced.

18. The process of claim 1, wherein said chlorofluorocompound comprises 2,3-dichloro-1,1,1,2-tetrafluoropropane.

19. The process of claim 18, wherein 2,3,3,3-tetrafluoro-1-propene is produced.

20. The process of claim 1, wherein said chlorofluorocompound comprises 1-chloro-1,2,2,3-tetrafluoropropane.

21. The process of claim 20, wherein 1,2,3-trifluoropropene is produced.

22. The process of claim 1, wherein said chlorofluorocompound comprises 3-chloro-1,1,2,2-tetrafluoropropane.

23. The process of claim 22, wherein 2,3,3-trifluoro-1-propene is produced.

* * * * *